United States Patent [19]

Murdock

[11] 4,410,524

[45] Oct. 18, 1983

[54] NOVEL 1,4-BIS(SUBSTITUTED-AMINO)-5,8-DIHYDROXYANTHRAQUINONES AND LEUCO BASES THEREOF

[75] Inventor: Keith C. Murdock, Pearl River, N.Y.

[73] Assignee: American Cyanamid Company, Stamford, Conn.

[21] Appl. No.: 383,363

[22] Filed: Jun. 1, 1982

[51] Int. Cl.$^3$ .................. A61K 31/42; A61K 31/535; C07D 263/06; C07D 265/06
[52] U.S. Cl. .......................... 424/248.51; 424/248.56; 424/263; 424/272; 544/72; 546/256; 548/215
[58] Field of Search .......................... 544/72; 546/256; 548/215; 424/248.51, 248.56, 263, 272

[56] References Cited

U.S. PATENT DOCUMENTS 4,197,249  4/1980  Murdock et al. .................. 260/380
4,296,030  10/1981  Lang et al. ...................... 260/380 X Primary Examiner—Richard Raymond
Attorney, Agent, or Firm—E. A. Conroy

[57] ABSTRACT

This disclosure describes novel 1,4,-bis(substituted-amino)-5,8-dihydroxyanthraquinones and leuco bases thereof, useful as chelating agents and for inhibiting the growth of transplanted mouse tumors. This disclosure also describes compositions of matter useful as inhibitors of transplanted mouse tumor growth and the method of inducing the regression and/or palliation of leukemia and related cancers in mammals therewith.

37 Claims, No Drawings

NOVEL 1,4-BIS(SUBSTITUTED-AMINO)-5,8-DIHYDROXYANTHRAQUINONES AND LEUCO BASES THEREOF

BRIEF SUMMARY OF THE INVENTION

This invention relates to new organic compounds and, more particularly is concerned with novel 1,4-bis-(substituted-amino)-5,8-dihydroxyanthraquinones which may be represented by the following general formula:

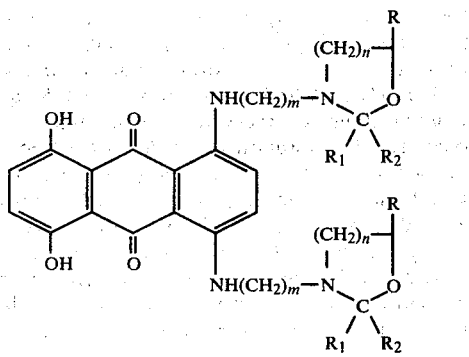

wherein m is the integer 2 or 3; n is the integer 1 or 2; R is hydrogen or methyl; $R_1$ is hydrogen or methyl; and $R_2$ is alkyl ($C_1$–$C_6$), ethenyl, 2-pyridyl, 3-pyridyl, 4-pyridyl, 2-thienyl, 3-thienyl, 2-furyl, 3-furyl, 2-pyrrolyl, 3-pyrrolyl, 1-naphthyl, 2-naphthyl, pentafluorophenyl or moieties of the formula:

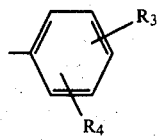

wherein $R_3$ and $R_4$ are each individually selected from the group consisting of hydrogen, fluoro, chloro, bromo, hydroxy, methyl, methoxy, benzyloxy, cyano, dimethylamino, nitro and trifluoromethyl; and $R_1$ and $R_2$ taken together comprise an alkylene group —(CH$_2$-)$_p$—, where p is an integer from 2 to 6, inclusive.

Also included within the purview of the present invention are the leuco bases and tautomers thereof which may be represented by the following general formulae:

(II, Leuco Bases)

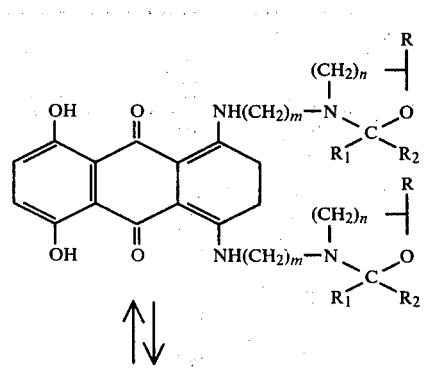

(III, Tautomer Form)

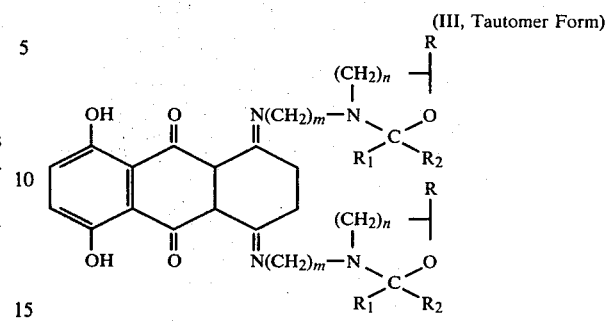

wherein R, $R_1$, $R_2$ m and n are as hereinbefore defined.

DETAILED DESCRIPTION OF THE INVENTION

The free bases (I) of the present invention are obtainable as blue, blue-black or orange-brown crystalline materials having characteristic melting points and absorption spectra and which are generally soluble in organic solvents such as chloroform, ethyl acetate, dichloromethane, hot benzene or toluene and the like, and may be purified by crystallization from these solvents or by leaching. The organic bases of this invention (I) form acid-addition salts with a variety of pharmacologically acceptable organic and inorganic salt-forming reagents. Thus, acid-addition salts, formed by admixture of the organic free base with one or two equivalents of an acid, suitably in a neutral sovlent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention, the free bases are equivalent to their acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention may be readily prepared in accordance with the following reaction scheme:

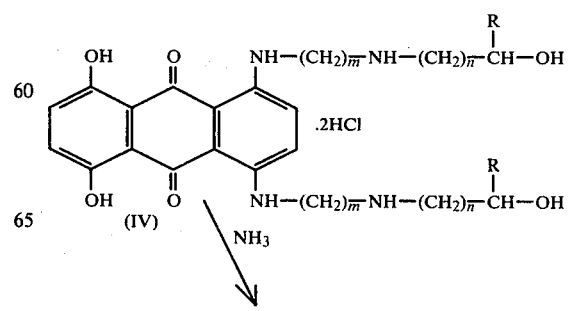

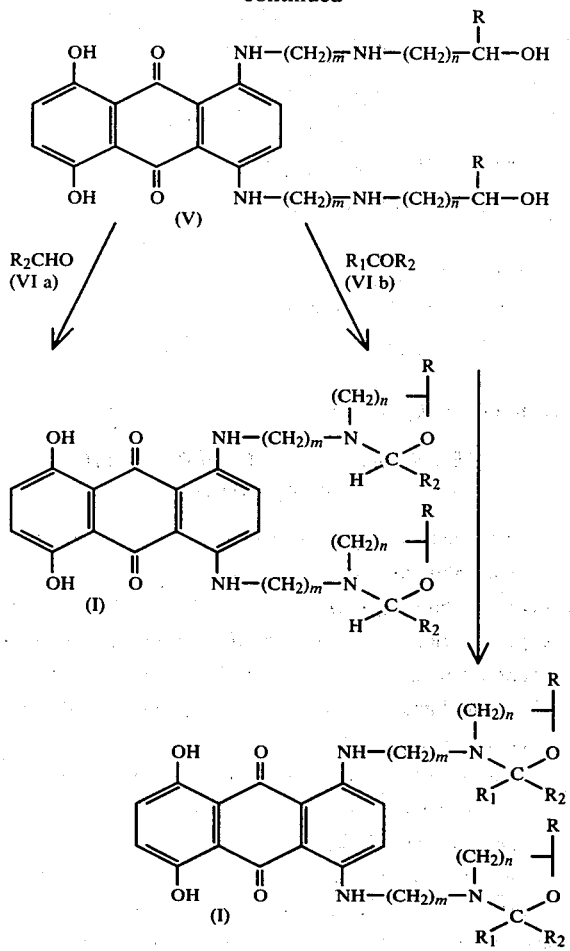

where R, $R_1$, $R_2$, m and n are as previously defined. In accordance with the above reaction scheme, a 1,4-dihydroxy-5,8-bis[[(hydroxyalkylamino)alkyl]amino]anthraquinone dihydrochloride (IV) in a solvent such as methanol is cooled at 0°–20° C. and saturated with ammonia gas to yield the corresponding free base (V). A suspension of the free base (7 mmol.) (V) in benzene or toluene (35–60 ml.) containing an aldehyde (VIa) (21 mmol.) such as acetaldehyde, butyraldehyde, acrolein, benzaldehyde, p-anisaldehyde, 2-hydroxy-p-anisaldehyde, 3,5-dimethoxybenzaldehyde, 2-pyridinecarboxaldehyde, 2-thiophenecarboxaldehyde, pyrrole-2-carboxaldehyde, 2-furaldehyde, 4-benzyloxybenzaldehyde, naphthaldehyde and the like or a ketone (VIb) (21 mmol.) such as acetone or cyclohexanone and the like is stirred and heated under reflux for 2–48 hours using a Dean-Stark trap or molecular sieves to remove by-product water from the distillate. Undissolved solid is removed by filtration and the desired product (I) is crystallized by concentration of the filtrate and/or by adding a solvent such as ether, petroleum ether, methanol and the like and allowing the mixture to stand at room temperature for several hours to several days.

The novel compounds described herein are useful as chelating, complexing or sequestering agents. The complexes formed with polyvalent metal ions are particularly stable and usually soluble in various organic solvents. These properties, of course, render them useful for a variety of purposes wherein metal ion contamination presents a problem; e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by these materials and as metal carriers. Other uses common to sequestering agents are also apparent for these compounds.

The novel compounds of the present invention also possess the property of inhibiting the growth of transplanted mouse tumors as established by the following tests.

LYMPHOCYTIC LEUKEMIA P388 TEST

The animals used are $BDF_1$ mice all of one sex, weighing a minimum of 17 g. and all within a 3 g. weight range. There are 5 or 6 animals per test group. The tumor transplant is by intraperitoneal injection of 0.5 ml. of dilute ascitic fluid containing $10^6$ cells of lymphocytic leukemia P388. The test compounds are administered intraperitoneally on days one, 5 and 9 (relative to tumor inoculation) at various doses. The animals are weighed and survivors are recorded on a regular basis for 30 days. The median survival time and the ratio of survival time for treated (T)/control (C) animals are calculated. The positive control compound is 1,4-dihydroxy-5,8-bis-[[2-(2-hydroxyethylamino)ethyl]amino]anthraquinone dihydrochloride, [U.S. Pat. No. 4,197,249; claim 19] given as a 0.025, 0.1, 0.2 or 0.4 mg./kg. injection, or the bis-(2-imidazolin-2-ylhydrazone) of 9,10-anthracenedicarboxaldehyde dihydrochloride [U.S. Pat. No. 4,258,181; claim 2] given as a 0.2, 0.8, or 3.0 mg./kg. injection. The results of this test with representative compounds of the present invention appear in Table I. The criterion for efficacy is $T/C \times 100 \geq 125\%$.

TABLE I

| Lymphocytic Leukemia P388 Test | | | |
|---|---|---|---|
| Compound | Dose mg./kg. | Median Survival Time (Days) | T/C × 100 (Percent) |
| 1,4-Dihydroxy-5,8-bis[[2-(2-phenyloxazolidin-3-yl)ethyl]amino]anthraquinone | 50 | 20.5 | 167 |
| | 12 | 22.5 | 183 |
| | 3 | 32 | 260 |
| | 0.8 | 30 | 244 |
| | 0.2 | 17 | 138 |
| Control | | 12.3 | |
| 1,4-Dihydroxy-5,8-bis[[2-(2-hydroxyethylamino)ethyl]amino]anthraquinone dihydrochloride | 0.1 | 18.5 | 150 |
| 1,4-Dihydroxy-5,8-bis[[2-(1-oxa-4-azaspiro[4.5]dec-4-yl)ethyl]amino]anthraquinone | 12 | >30 | >273 |
| | 3 | 20 | 182 |
| | 0.8 | 20.5 | 186 |
| | 0.2 | 16.5 | 150 |

TABLE I-continued

Lymphocytic Leukemia P388 Test

| Compound | Dose mg./kg. | Median Survival Time (Days) | T/C × 100 (Percent) |
|---|---|---|---|
| | 0.05 | 16 | 145 |
| Control | | 11.0 | |
| 1,4-Dihydroxy-5,8-bis[[2-(2-hydroxyethylamino)-ethyl]amino]anthraquinone dihydrochloride | 0.1 | 27 | 245 |
| 1,4-Bis[[2-(2,2-dimethyl-3-oxazolidinyl)ethyl]-amino]-5,8-dihydroxyanthraquinone | 12 | >30 | >273 |
| | 3 | >30 | >273 |
| | 0.8 | >25.5 | >232 |
| | 0.2 | 19.5 | 177 |
| | 0.05 | 18 | 164 |
| Control | | 11.0 | |
| 1,4-Dihydroxy-5,8-bis[[2-(2-hydroxyethylamino)-ethyl]amino]anthraquinone dihydrochloride | 0.1 | 27 | 245 |
| 1,4-Bis[[2-(2-furyl)-3-oxazolidinyl]ethyl]-amino]-5,8-dihydroxyanthraquinone (1st test) | 200 | 24 | 240 |
| | 50 | 23 | 230 |
| | 12 | 25 | 250 |
| | 3 | 21.5 | 215 |
| | 0.8 | 21.0 | 210 |
| Control | | 10.0 | |
| 1,4-Dihydroxy-5,8-bis[[2-(2-hydroxyethylamino)-ethyl]amino]anthraquinone dihydrochloride | 0.2 | 22.5 | 225 |
| 1,4-Bis[[2-[2-(2-furyl)-3-oxazolidinyl]ethyl]-amino]-5,8-dihydroxyanthraquinone (2nd test) | 6.4 | >28 | >272 |
| | 1.6 | 21.5 | 209 |
| | 0.4 | 20 | 194 |
| | 0.1 | 19 | 184 |
| | 0.025 | 16.5 | 160 |
| Control | | 10.3 | |
| 1,4-Dihydroxy-5,8-bis[[2-(2-hydroxyethylamino)-ethyl]amino]anthraquinone dihydrochloride | 0.1 | 17.5 | 170 |
| 1,4-Dihydroxy-5,8-bis[[2-(2-propyl-3-oxazolidi-nyl)ethyl]amino]anthraquinone (1st test) | 12 | 14 | 147 |
| | 3 | 25 | 263 |
| | 0.8 | 23 | 242 |
| Control | | 9.5 | |
| 1,4-Dihydroxy-5,8-bis[[2-(2-hydroxyethylamino)-ethyl]amino]anthraquinone | 0.2 | 14.5 | 153 |
| 1,4-Dihydroxy-5,8-bis[[2-(2-propyl-3-oxazolidi-nyl)ethyl]amino]anthraquinone (2nd test) | 12 | 16.5 | 160 |
| | 3 | 15.0 | 146 |
| | 0.8 | 14.0 | 136 |
| Control | | 10.3 | |
| 1,4-Dihydroxy-5,8-bis[[2-(2-hydroxyethylamino)-ethyl]amino]anthraquinone dihydrochloride | 0.1 | 17.5 | 170 |
| 1,4-Dihydroxy-5,8-bis[[2-(2-methyloxazolidin-3-yl)ethyl]amino]anthraquinone | 6.4 | 24 | 233 |
| | 1.6 | 22 | 214 |
| | 0.4 | 21 | 204 |
| | 0.1 | 17.5 | 170 |
| | 0.025 | 15.5 | 150 |
| Control | | 10.3 | |
| 1,4-Dihydroxy-5,8-bis[[2-(2-hydroxyethylamino)-ethyl]amino]anthraquinone dihydrochloride | 0.1 | 17.5 | 170 |
| 1,4-Bis[[2-(2-hexyl-3-oxazolidinyl)ethyl]amino]-5,8-dihydroxyanthraquinone (1st test) | 50 | 16 | 157 |
| | 12 | >30 | >294 |
| | 3 | >30 | >294 |
| | 0.8 | 24.5 | 240 |
| | 0.2 | 23 | 225 |
| Control | | 10.2 | |
| 1,4-Dihydroxy-5,8-bis[[2-(2-hydroxyethylamino)-ethyl]amino]anthraquinone dihydrochloride | 0.1 | 16 | 157 |
| 1,4-Bis[[2-(2-hexyl-3-oxazolidinyl)ethyl]amino-]-5,8-dihydroxyanthraquinone (2nd test) | 1.6 | >30 | >300 |
| | 0.4 | 17.5 | 175 |
| | 0.1 | 17 | 170 |
| | 0.025 | 15 | 150 |
| | .006 | 13 | 130 |
| Control | | 10.0 | |
| 1,4-Dihydroxy-5,8-bis[[2-(2-hydroxyethylamino)-ethyl]amino]anthraquinone dihydrochloride | 0.1 | 23 | 230 |
| 1,4-Dihydroxy-5,8-bis[[2-[2-(p-methoxyphenyl)-3-oxazolidinyl]ethyl]amino]anthraquinone (1st test) | 200 | >30 | >294 |
| | 50 | >30 | >294 |
| | 12 | >30 | >294 |
| | 3 | >30 | >294 |
| | 0.8 | 23 | 225 |
| | 0.2 | 25 | 245 |
| Control | | 10.2 | |
| 1,4-Dihydroxy-5,8-bis[[2-(2-hydroxyethylamino)-ethyl]amino]anthraquinone dihydrochloride | 0.1 | 16 | 157 |
| 1,4-Dihydroxy-5,8-bis[[2-[2-(p-methoxyphenyl)-3-oxazolidinyl]ethyl]amino]anthraquinone (2nd test) | 1.6 | 20 | 200 |
| | 0.4 | 16 | 160 |
| | 0.1 | 14.5 | 145 |
| Control | | 10.0 | |
| 1,4-Dihydroxy-5,8-bis[[2-(2-hydroxyethylamino)- | 0.1 | 23 | 230 |

TABLE I-continued

Lymphocytic Leukemia P388 Test

| Compound | Dose mg./kg. | Median Survival Time (Days) | T/C × 100 (Percent) |
|---|---|---|---|
| ethyl]amino]anthraquinone dihydrochloride | | | |
| 1,4-Dihydroxy-5,8-bis[[2-[2-(2-pyridyl)-3-oxazol- | 50 | 19 | 186 |
| idinyl]ethyl]amino]anthraquinone | 12 | 25.5 | 250 |
| (1st test) | 3 | >30 | >294 |
| | 0.8 | >28 | >275 |
| | 0.2 | 22 | 215 |
| Control | | 10.2 | |
| 1,4-Dihydroxy-5,8-bis[[2-(2-hydroxyethylamino)- | 0.1 | 16 | 157 |
| ethyl]amino]anthraquinone dihydrochloride | | | |
| 1,4-Dihydroxy-5,8-bis[[2-[2-(2-pyridyl)-3-oxazol- | 1.6 | >28 | >280 |
| idinyl]ethyl]amino]anthraquinone | 0.4 | 24.5 | 245 |
| (2nd test) | 0.1 | 15.5 | 155 |
| | 0.025 | 12.5 | 125 |
| Control | | 10.0 | |
| 1,4-Dihydroxy-5,8-bis[[2-(2-hydroxyethylamino)- | 0.1 | 23 | 230 |
| ethyl]amino]anthraquinone dihydrochloride | | | |
| 1,4-Dihydroxy-5,8-bis[[2-[2-(3-pyridyl)-3-oxazol- | 50 | 19 | 186 |
| idinyl]ethyl]amino]anthraquinone | 12 | >30 | >294 |
| (1st test) | 3 | >25 | >245 |
| | 0.8 | >27 | >264 |
| | 0.2 | 22.5 | 221 |
| Control | | 10.2 | |
| 1,4-Dihydroxy-5,8-bis[[2-(2-hydroxyethylamino)- | 0.1 | 16 | 157 |
| ethyl]amino]anthraquinone dihydrochloride | | | |
| 1,4-Dihydroxy-5,8-bis[[2-[2-(3-pyridyl)-3-oxazol- | 1.6 | 19.5 | 195 |
| idinyl]ethyl]amino]anthraquinone | 0.4 | 18 | 180 |
| (2nd test) | 0.1 | 17 | 170 |
| | 0.025 | 13.5 | 135 |
| | 0.006 | 13 | 130 |
| Control | | 10.0 | |
| 1,4-Dihydroxy-5,8-bis[[2-(2-hydroxyethylamino)- | 0.1 | 23 | 230 |
| ethyl]amino]anthraquinone dihydrochloride | | | |
| 1,4-Bis[[2-[2-(p-fluorophenyl)-3-oxazolidinyl]- | 50 | 13 | 127 |
| ethyl]amino]-5,8-dihydroxyanthraquinone | 12 | >24 | >235 |
| (1st test) | 3 | 24 | 235 |
| | 0.8 | 21 | 206 |
| | 0.2 | 17 | 167 |
| Control | | 10.2 | |
| 1,4-Dihydroxy-5,8-bis[[2-(2-hydroxyethylamino)- | 0.1 | 23 | 225 |
| ethyl]amino]anthraquinone dihydrochloride | | | |
| 1,4-Bis[[2-[2-(p-fluorophenyl)-3-oxazolidinyl]- | 12 | 23 | 209 |
| ethyl]amino]-5,8-dihydroxyanthraquinone | 3 | 16 | 145 |
| (2nd test) | | | |
| Control | | 11.0 | |
| 1,4-Dihydroxy-5,8-bis[[2-(2-hydroxyethylamino)- | 0.1 | 16 | 145 |
| ethyl]amino]anthraquinone dihydrochloride | | | |
| 1,4-Dihydroxy-5,8-bis[[2-[2-(2-hydroxy-4-methoxy- | 50 | 27 | 252 |
| phenyl)-3-oxazolidinyl]ethyl]amino]anthraquinone | 12 | >30 | >280 |
| | 3 | >29 | >271 |
| | 0.8 | 27 | 252 |
| Control | | 10.7 | |
| 1,4-Dihydroxy-5,8-bis[[2-(2-hydroxyethylamino)- | 0.1 | 26 | 243 |
| ethyl]amino]anthraquinone dihydrochloride | | | |
| 1,4-Bis[[2-[2-[p-(benzyloxy)phenyl]-3-oxazolidi- | 200 | >28 | >262 |
| nyl]ethyl]amino]-5,8-dihydroxyanthraquinone | 50 | >30 | >280 |
| (1st test) | 12 | >30 | >280 |
| | 3 | 22 | 206 |
| | 0.8 | 20 | 187 |
| Control | | 10.7 | |
| 1,4-Dihydroxy-5,8-bis[[2-(2-hydroxyethylamino)- | 0.1 | 26 | 243 |
| ethyl]amino]anthraquinone dihydrochloride | | | |
| 1,4-Bis[[2-[2-[p-(benzyloxy)phenyl]-3-oxazolidi- | 6.4 | 21.5 | 215 |
| nyl]ethyl]amino]-5,8-dihydroxyanthraquinone | 1.6 | 22 | 220 |
| (2nd test) | 0.4 | 17 | 170 |
| | 0.1 | 17.5 | 175 |
| | 0.025 | 16 | 160 |
| Control | | 10.0 | |
| 1,4-Dihydroxy-5,8-bis[[2-(2-hydroxyethylamino)- | 0.025 | 16 | 160 |
| ethyl]amino]anthraquinone dihydrochloride | | | |
| 1,4-Bis[[2-[2-(2,4-dimethoxyphenyl)-3-oxazolidi- | 50 | 22 | 206 |
| nyl]ethyl]amino]-5,8-dihydroxyanthraquinone | 12 | 22 | 206 |
| (1st test) | 3 | 21 | 196 |
| | 0.8 | 17.5 | 164 |
| Control | | 10.7 | |
| 1,4-Dihydroxy-5,8-bis[[2-(2-hydroxyethylamino)- | 0.1 | 26 | 243 |
| ethyl]amino]anthraquinone dihydrochloride | | | |
| 1,4-Bis[[2-[2-(2,4-dimethoxyphenyl)-3-oxazolidi- | 6.4 | 26.5 | 265 |
| nyl]ethyl]amino]-5,8-dihydroxyanthraquinone | 1.6 | 20 | 200 |

TABLE I-continued

Lymphocytic Leukemia P388 Test

| Compound | Dose mg./kg. | Median Survival Time (Days) | T/C × 100 (Percent) |
|---|---|---|---|
| (2nd test) | 0.4 | 18 | 180 |
| | 0.1 | 17 | 170 |
| Control | | 10.0 | |
| 1,4-Dihydroxy-5,8-bis[[2-(2-hydroxyethylamino)-ethyl]amino]anthraquinone dihydrochloride | 0.025 | 16 | 160 |
| 1,4-Bis[[2-[2-(3,5-dimethoxyphenyl)-3-oxazolidinyl]ethyl]amino-5,8-dihydroxyanthraquinone | 50 | 16 | 145 |
| | 12 | 17 | 155 |
| (1st test) | 3 | 18 | 164 |
| Control | | 11.0 | |
| 1,4-Dihydroxy-5,8-bis[[2-(2-hydroxyethylamino)-ethyl]amino]anthraquinone dihydrochloride | 0.1 | 16.0 | 145 |
| 1,4-Bis[[2-[2-(3,5-dimethoxyphenyl)-3-oxazolidinyl]ethyl]amino]-5,8-dihydroxyanthraquinone | 50 | >30 | >244 |
| | 12 | >30 | >244 |
| (2nd test) | 3 | 26 | 211 |
| | 0.8 | 20 | 163 |
| | 0.2 | 16 | 130 |
| Control | | 12.3 | |
| 1,4-Dihydroxy-5,8-bis[[2-(2-hydroxyethylamino)-ethyl]amino]anthraquinone dihydrochloride | 0.1 | 18.5 | 150 |
| 1,4-Dihydroxy-5,8-bis[[2-[2-(1-naphthyl)-3-oxazolidinyl]ethyl]amino]anthraquinone | 1.6 | >25.5 | >232 |
| | 0.4 | 24.5 | 223 |
| (1st test) | 0.1 | 16.5 | 150 |
| Control | | 11.0 | |
| Bis(2-imidazolin-2-ylhydrazone) of 9,10-anthracenedicarboxaldehyde dihydrochloride | 0.8 | 16.0 | 145 |
| 1,4-Dihydroxy-5,8-bis[[2-[2-(1-naphthyl)-3-oxazolidinyl]ethyl]amino]anthraquinone | 3.2 | >30 | >273 |
| | 0.8 | 26 | 236 |
| (2nd test) | 0.2 | 21 | 191 |
| | 0.05 | 14 | 127 |
| Control | | 11.0 | |
| Bis(2-imidazolin-2-ylhydrazone) of 9,10-anthracenedicarboxaldehyde dihyrochloride | 0.8 | 17.5 | 159 |
| 1,4-Dihydroxy-5,8-bis[[2-[2-(4-pyridyl)-3-oxazolidinyl]ethyl]amino]anthraquinone | 100 | >30 | >244 |
| | 25 | >30 | >244 |
| | 6 | >30 | >244 |
| | 1.5 | 19 | 154 |
| | 0.4 | 19 | 154 |
| | 0.1 | 18.5 | 150 |
| Control | | 12.3 | |
| 1,4-Dihydroxy-5,8-bis[[2-(2-hydroxyethylamino)-ethyl]amino]anthraquinone dihydrochloride | 0.1 | 18.5 | 150 |
| 1,4-Dihydroxy-5,8-bis[[2-[2-(4-pyridyl)-3-oxazolidinyl]ethyl]amino]anthraquinone | 1.6 | 18.5 | 168 |
| | 0.4 | 16.5 | 149 |
| (2nd test) Control | | 11.0 | |
| 1,4-Dihydroxy-5,8-bis[[2-(2-hydroxyethylamino)-ethyl]amino]anthraquinone dihydrochloride | 0.025 | 15.5 | 141 |
| 1,4-Dihydroxy-5,8-bis[[2-[2-(pentafluorophenyl)-3-oxazolidinyl]ethyl]amino]anthraquinone | 200 | 15.5 | 138 |
| | 50 | >30 | >268 |
| (1st test) | 12 | >29 | >259 |
| | 3 | 27.5 | 246 |
| Control | | 11.2 | |
| 1,4-Dihydroxy-5,8-bis[[2-(2-hydroxyethylamino)-ethyl]amino]anthraquinone dihydrochloride | 0.4 | 23.5 | 210 |
| 1,4-Dihydroxy-5,8-bis[[2-[2-(pentafluorophenyl)-3-oxazolidinyl]ethyl]amino]anthraquinone | 50 | >30 | >300 |
| | 12 | >30 | >300 |
| (2nd test) | 3 | 30 | 300 |
| | 0.8 | 12.5 | 125 |
| Control | | 10.0 | |
| 1,4-Dihydroxy-5,8-bis[[2-(2-hydroxyethylamino)-ethyl]amino]anthraquinone dihydrochloride | 0.1 | 25 | 250 |
| 1,4-Bis[[2-[2-(2-chloro-5-nitrophenyl)-3-oxazolidinyl]ethyl]amino]-5,8-dihydroxyanthraquinone | 100 | >30 | >283 |
| | 25 | >30 | >283 |
| (1st test) | 6 | 16 | 151 |
| Control | | 10.6 | |
| 1,4-Dihydroxy-5,8-bis[[2-(2-hydroxyethylamino)-ethyl]amino]anthraquinone dihydrochloride | 0.1 | 16.5 | 156 |
| 1,4-Bis[[2-[2-(2-chloro-5-nitrophenyl)-3-oxazolidinyl]ethyl]amino]-5,8-dihydroxyanthraquinone | 25 | >30 | >300 |
| | 6 | 16 | 160 |
| (2nd test) | 1.5 | 11 | 110 |
| Control | | 10.0 | |
| 1,4-Dihydroxy-5,8-bis[[2-(2-hydroxyethylamino)-ethyl]amino]anthraquinone dihydrochloride | 0.025 | 13 | 130 |
| 1,4-Bis[[2-[2-(5-chloro-2-nitrophenyl)-3-oxazolidinyl]ethyl]amino]-5,8-dihydroxyanthraquinone | 200 | 11 | 104 |
| | 50 | 15 | 142 |
| (1st test) | 12 | 23 | 217 |
| | 3 | 18 | 170 |
| Control | | 10.6 | |

TABLE I-continued

Lymphocytic Leukemia P388 Test

| Compound | Dose mg./kg. | Median Survival Time (Days) | T/C × 100 (Percent) |
|---|---|---|---|
| 1,4-Dihydroxy-5,8-bis[[2-(2-hydroxyethylamino)-ethyl]amino]anthraquinone dihydrochloride | 0.1 | 16.5 | 156 |
| 1,4-Bis[[2-[2-(5-chloro-2-nitrophenyl)-3-oxazolidinyl]ethyl]amino]-5,8-dihydroxyanthraquinone | 25 | >30 | >300 |
|  | 6 | >25 | >250 |
| (2nd test) | 1.5 | 13.5 | 135 |
| Control |  | 10.0 |  |
| 1,4-Dihydroxy-5,8-bis[[2-(2-hydroxyethylamino)-ethyl]amino]anthraquinone dihydrochloride | 0.025 | 13 | 130 |
| 1,4-Bis[[2-[2-(2,6-dichlorophenyl)-3-oxazolidinyl]ethyl]amino-5,8-dihydroxyanthraquinone | 200 | 22 | 220 |
|  | 50 | >30 | >300 |
| (1st test) | 12 | >29 | >290 |
|  | 3 | 12 | 120 |
| Control |  | 10.0 |  |
| 1,4-Dihydroxy-5,8-bis[[2-(2-hydroxyethylamino)-ethyl]amino]anthraquinone dihydrochloride | 0.1 | 15 | 150 |
| 1,4-Bis[[2-[2-(2,6-dichlorophenyl)-3-oxazolidinyl]ethyl]amino]-5,8-dihydroxyanthraquinone | 25 | >30 | >261 |
|  | 12 | 23.5 | 204 |
| (2nd test) | 6 | 17 | 148 |
|  | 3 | 13.5 | 118 |
| Control |  | 11.5 |  |
| 1,4-Dihydroxy-5,8-bis[[2-(2-hydroxyethylamino)-ethyl]amino]anthraquinone dihydrochloride | 0.2 | 16 | 139 |
| 1,4-Dihydroxy-5,8-bis[[2-[2-(2-methylphenyl)-3-oxazolidinyl]ethyl]amino]anthraquinone | 50 | 8.5 | 85 |
|  | 12 | 16.5 | 165 |
| (1st test) | 3 | 27.5 | 275 |
| Control |  | 10.0 |  |
| 1,4-Dihydroxy-5,8-bis[[2-(2-hydroxyethylamino)-ethyl]amino]anthraquinone dihydrochloride | 0.1 | 15 | 150 |
| 1,4-Dihydroxy-5,8-bis[[2-[2-(2-methylphenyl)-3-oxazolidinyl]ethyl]amino]anthraquinone | 12 | >29 | >252 |
|  | 6 | >30 | >261 |
| (2nd test) | 3 | 14.5 | 126 |
|  | 1.5 | 16.5 | 143 |
| Control |  | 11.5 |  |
| 1,4-Dihydroxy-5,8-bis[[2-(2-hydroxyethylamino)-ethyl]amino]anthraquinone dihydrochloride | 0.2 | 16 | 139 |
| 1,4-Bis[[2-[2-(3-bromophenyl)-3-oxazolidinyl]-ethyl]amino]-5,8-dihydroxyanthraquinone | 200 | 10.5 | 105 |
|  | 50 | 15.5 | 155 |
| (1st test) | 12 | >30 | >300 |
|  | 3 | >28 | >280 |
| Control |  | 10.0 |  |
| 1,4-Dihydroxy-5,8-bis[[2-(2-hydroxyethylamino)-ethyl]amino]anthraquinone dihydrochloride | 0.1 | 15 | 150 |
| 1,4-Bis[[2-[2-(3-bromophenyl)-3-oxazolidinyl]-ethyl]amino]-5,8-dihydroxyanthraquinone | 12 | >30 | >261 |
|  | 6 | 24 | 209 |
| (2nd test) | 3 | 23 | 200 |
|  | 1.5 | 14 | 122 |
|  | 0.8 | 14.5 | 126 |
| Control |  | 11.5 |  |
| 1,4-Dihydroxy-5,8-bis[[2-(2-hydroxyethylamino)-ethyl]amino]anthraquinone dihydrochloride | 0.2 | 16 | 139 |
| 1,4-Dihydroxy-5,8-bis[[2-[2-[3-(trifluoromethyl)phenyl]-3-oxazolidinyl]ethyl]amino]-anthraquinone | 50 | >22.5 | >236 |
|  | 12 | >30 | >315 |
| (1st test) | 3 | 24 | 253 |
| Control |  | 9.5 |  |
| 1,4-Dihydroxy-5,8-bis[[2-(2-hydroxyethyl-amino)ethyl]amino]anthraquinone dihydrochloride | 0.1 | 18.5 | 195 |
| 1,4-Dihydroxy-5,8-bis[[2-[2-[3-(trifluoromethyl)phenyl]-3-oxazolidinyl]ethyl]amino]-anthraquinone | 1.6 | 19 | 173 |
|  | 0.4 | 20 | 182 |
|  | 0.1 | 14.5 | 132 |
| (2nd test) | 0.025 | 14 | 127 |
| Control |  | 11.0 |  |
| 1,4-Bis[[2-[2-[4-(dimethylamino)phenyl]-3-oxazolidinyl]ethyl]amino]-5,8-dihydroxy-anthraquinone | 3 | >30 | >286 |
|  | 0.8 | >30 | >286 |
|  | 0.2 | >28 | >267 |
| (1st test) |  |  |  |
| Control |  | 10.5 |  |
| 1,4-Dihydroxy-5,8-bis[[2-(2-hydroxyethyl-amino)ethyl]amino]anthraquinone dihydrochloride | 0.8 | >30 | >286 |
| 1,4-Bis[[2-[2-[4-(dimethylamino)phenyl]-3-oxazolidinyl]ethyl]amino]-5,8-dihydroxy-anthraquinone | 3 | >30 | >291 |
|  | 1.5 | >30 | >291 |
|  | 0.8 | 21.0 | 204 |
| (2nd test) | 0.4 | 20 | 194 |
| Control |  | 10.3 |  |
| 1,4-Dihydroxy-5,8-bis[[2-[2-hydroxyethyl-amino)ethyl]amino]anthraquinone dihydro- | 0.1 | 16.5 |  |

| Compound | Dose mg./kg. | Median Survival Time (Days) | T/C × 100 (Percent) |
|---|---|---|---|
| chloride | | | |

MELANOTIC MELANOMA B16

The animals used are BDF₁ mice, all of the same sex, weighing a minimum of 17 g. and all within a 3 g. weight range. There are normally 6 animals per test group. A one-gram portion of melanotic melanoma B16 tumor is homogenized in 10 ml. of cold balanced salt solution and a 0.5 ml. aliquot of the homogenate is implanted intraperitoneally into each of the test mice. The test compounds are administered intraperitoneally on days one through 9 (relative to tumor inoculation) at various doses. The animals are weighed and survivors are recorded on a regular basis for 60 days. The median survival time and the ratio of survival time for treated (T)/control (C) animals are calculated. The positive control compound is 1,4-dihydroxy-5,8-bis[[2-(2-hydroxyethylamino)ethyl]amino]anthraquinone dihydrochloride, [U.S. Pat. No. 4,197,249; claim 19] given as a 0.05, 0.1, 0.2, 0.4, 1.6 or 6.4 mg./kg. injection. The results of this test with representative compounds of the present invention appear in Table II. The criterion for efficacy is T/C × 100 ≧ 125%.

TABLE II

Melanotic Melanoma B16

| Compound | Dose mg./kg. | Median Survival Time (Days) | T/C × 100 (Percent) |
|---|---|---|---|
| 1,4-Dihydroxy-5,8-bis[[2-(1-oxa-4-azaspiro[4.5]dec-4-yl)-ethyl]amino]anthraquinone | 25 | 36 | 180 |
|  | 12 | 36 | 180 |
| (1st test) | 6 | 35 | 175 |
| Control |  | 20.0 |  |
| 1,4-Dihydroxy-5,8-bis[[2-(2-hydroxyethylamino)ethyl]-amino]anthraquinone dihydrochloride | 6.4 | 40 | 200 |
| 1,4-Dihydroxy-5,8-bis[[2-(1-oxa-4-azaspiro[4.5]dec-4-yl)-ethyl]amino]anthraquinone | 12 | 29.5 | 142 |
|  | 6 | 28 | 135 |
| (2nd test) | 3 | 60 | >288 |
|  | 1.5 | 58 | >279 |
| Control |  | 20.8 |  |
| 1,4-Dihydroxy-5,8-bis[[2-(2-hydroxyethylamino)ethyl]-amino]anthraquinone dihydrochloride | 0.05 | 39 | >188 |
| 1,4-Bis[[2-(2,2-dimethyl-3-oxazolidinyl)ethyl]amino]-5,8-dihydroxyanthraquinone | 6 | 32 | 160 |
| Control |  | 20.0 |  |
| 1,4-Dihydroxy-5,8-bis[[2-(2-hydroxyethylamino)ethyl]-amino]anthraquinone dihydrochloride | 6.4 | 40 | 200 |
| 1,4-Bis[[2-[2-(2-furyl)-3-oxazolidinyl]ethyl]amino-5,8-dihydroxyanthraquinone | 12 | 50 | 240 |
|  | 3 | >56 | >269 |
| (1st test) | 0.8 | 28 | 135 |
| Control |  | 20.8 |  |
| 1,4-Dihydroxy-5,8-bis[[2-(2-hydroxyethylamino)ethyl]-amino]anthraquinone dihydrochloride | 0.05 | 39 | >188 |
| 1,4-Bis[[2-[2-(2-furyl)-3-oxazolidinyl]ethyl]amino-5,8-dihydroxyanthraquinone | 12 | >60 | >286 |
|  | 6 | >60 | >286 |
| (2nd test) | 3 | 30 | 143 |
|  | 1.5 | 26 | 124 |
|  | 0.8 | 30 | 143 |
| Control |  | 21.0 |  |
| 1,4-Dihydroxy-5,8-bis[[2-(2-hydroxyethylamino)ethyl]-amino]anthraquinone dihydrochloride | 0.2 | 44.5 | 212 |
| 1,4-Dihydroxy-5,8-bis[[2-(2-propyl-3-oxazolidinyl)ethyl]-amino]anthraquinone | 12 | >53 | >262 |
|  | 3.2 | >60 | >297 |
| (1st test) | 0.8 | 34 | 168 |
|  | 0.2 | 36.5 | 181 |
| Control |  | 20.2 |  |
| 1,4-Dihydroxy-5,8-bis[[2-(2-hydroxyethylamino)ethyl]-amino]anthraquinone dihydrochloride | 0.2 | 32 | 158 |
| 1,4-Dihydroxy-5,8-bis[[2-(2-propyl-3-oxazolidinyl)ethyl]-amino]anthraquinone | 1.6 | 46 | 218 |
|  | 0.4 | 43 | 205 |
| (2nd test) | 0.1 | 29 | 138 |
|  | 0.025 | 27 | 129 |
| Control |  | 21.0 |  |
| 1,4-Dihydroxy-5,8-bis[[2-(2-hydroxyethylamino)ethyl]-amino]anthraquinone dihydrochloride | 0.2 | 44.5 | 212 |
| 1,4-Dihydroxy-5,8-bis[[2-(2-methyloxazolidin-3-yl)ethyl]-amino]anthraquinone | 3 | 32 | 156 |
|  | 0.8 | >50 | >244 |
|  | 0.2 | 34 | 166 |
| Control |  | 20.5 |  |
| 1,4-Dihydroxy-5,8-bis[[2-(2-hydroxyethylamino)ethyl]-amino]anthraquinone dihydrochloride | 0.2 | 32 | 156 |
| 1,4-Bis[[2-(2-hexyl-3-oxazolidinyl)ethyl]amino]-5,8-dihydroxyanthraquinone | 6 | 28 | 124 |
|  | 1.5 | 30 | 133 |

TABLE II-continued

Melanotic Melanoma B16

| Compound | Dose mg./kg. | Median Survival Time (Days) | T/C × 100 (Percent) |
|---|---|---|---|
| (1st test) | 0.4 | 33 | 147 |
| Control | | 22.5 | |
| 1,4-Dihydroxy-5,8-bis[[2-(2-hydroxyethylamino)ethyl]-amino]anthraquinone dihydrochloride | 0.1 | 35 | 156 |
| 1,4-Bis[[2-(2-hexyl-3-oxazolidinyl)ethyl]amino]-5,8-dihydroxyanthraquinone | 3 | >60 | >267 |
| | 0.8 | >60 | >267 |
| (2nd test) | 0.2 | 39.5 | 176 |
| Control | | 22.5 | |
| 1,4-Dihydroxy-5,8-bis[[2-(2-hydroxyethylamino)ethyl]-amino]anthraquinone dihydrochloride | 0.025 | 33.5 | 149 |
| 1,4-Dihydroxy-5,8-bis[[2-[2-(p-methoxyphenyl)-3-oxazolidinyl]ethyl]amino]anthraquinone | 6 | 34 | 151 |
| | 1.5 | 31 | 138 |
| (1st test) | 0.4 | 32 | 142 |
| Control | | 22.5 | |
| 1,4-Dihydroxy-5,8-bis[[2-(2-hydroxyethylamino)ethyl]-amino]anthraquinone dihydrochloride | 0.1 | 35 | 156 |
| 1,4-Dihydroxy-5,8-bis[[2-[2-(p-methoxyphenyl)-3-oxazolidinyl]ethyl]amino]anthraquinone | 3 | >60 | >267 |
| | 1.8 | >60 | >267 |
| (2nd test) | 0.2 | 26 | 116 |
| Control | | 22.5 | |
| 1,4-Dihydroxy-5,8-bis[[2-(2-hydroxyethylamino)ethyl]-amino]anthraquinone dihydrochloride | 0.025 | 33.5 | 149 |
| 1,4-Dihydroxy-5,8-bis[[2-[2-(2-pyridyl-3-oxazolidinyl]-ethyl]amino]anthraquinone | 6 | 39 | 173 |
| | 1.5 | 40 | 178 |
| (1st test) | 0.4 | 37 | 164 |
| Control | | 22.5 | |
| 1,4-Dihydroxy-5,8-bis[[2-(2-hydroxyethylamino)ethyl]-amino]anthraquinone dihydrochloride | 0.1 | 35 | 156 |
| 1,4-Dihydroxy-5,8-bis[[2-[2-(2-pyridyl)-3-oxazolidinyl]-ethyl]amino]anthraquinone | 0.8 | >60 | >267 |
| | 0.2 | 38 | 169 |
| (2nd test) | 0.05 | 37.5 | 167 |
| Control | | 22.5 | |
| 1,4-Dihydroxy-5,8-bis[[2-(2-hydroxyethylamino)ethyl]-amino]anthraquinone dihydrochloride | 0.025 | 33.5 | 149 |
| 1,4-Dihydroxy-5,8-bis[[2-[2-(3-pyridyl)-3-oxazolidinyl]-ethyl]amino]anthraquinone | 0.8 | >60 | >267 |
| | 0.2 | 41 | 182 |
| | 0.05 | 32 | 142 |
| Control | | 22.5 | |
| 1,4-Dihydroxy-5,8-bis[[2-(2-hydroxyethylamino)ethyl]-amino]anthraquinone dihydrochloride | 0.025 | 33.5 | 149 |
| 1,4-Bis[[2-[2-(p-fluorophenyl)-3-oxazolidinyl]ethyl]-amino[-5,8-dihydroxyanthraquinone | 25 | 29 | 129 |
| | 6 | 30 | 133 |
| | 1.5 | 30 | 133 |
| Control | | 22.5 | |
| 1,4-Dihydroxy-5,8-bis[[2-(2-hydroxyethylamino)ethyl]-amino]anthraquinone dihydrochloride | 0.1 | 35 | 156 |
| 1,4-Bis[[2-[2-(p-(benzyloxy)phenyl]-3-oxazolidinyl]ethyl]-amino]-5,8-dihydroxyanthraquinone | 6 | >60 | >268 |
| | *3 | >60 | >300 |
| | 1.5 | >59 | >263 |
| | *0.8 | 31 | 155 |
| Control | | 22.4 | |
| | | *20.0 | |
| 1,4-Dihydroxy-5,8-bis[[2-(2-hydroxyethylamino)ethyl]-amino]anthraquinone dihydrochloride | 0.1 | 34 | 152 |
| | *0.1 | 32 | 160 |
| 1,4-Bis[[2-[2-(2,4-dimethoxyphenyl)-3-oxazolidinyl]ethyl]-amino]-5,8-dihydroxyanthraquinone | 6 | >60 | >273 |
| | 1.5 | >60 | >273 |
| | 0.4 | 39 | 177 |
| Control | | 22.0 | |
| 1,4-Dihydroxy-5,8-bis[[2-(2-hydroxyethylamino)ethyl]-amino]anthraquinone dihydrochloride | 0.1 | 34 | 155 |
| 1,4-Bis[[2-[2-(3,5-dimethoxyphenyl)-3-oxazolidinyl]ethyl]-amino]-5,8-dihydroxyanthraquinone | 3 | >60 | >293 |
| | 0.8 | 30 | 146 |
| | 0.2 | 29 | 141 |
| | 0.05 | 28 | 137 |
| Control | | 20.5 | |
| 1,4-Dihydroxy-5,8-bis[[2-(2-hydroxyethylamino)ethyl]-amino]anthraquinone dihydrochloride | 0.1 | 30 | 146 |
| 1,4-Dihydroxy-5,8-bis[[2-[2-(1-naphthyl-3-oxazolidinyl]-ethyl]amino]anthraquinone | 12 | 32 | 158 |
| | 3 | >60 | >296 |
| (1st test) | 0.8 | 30 | 148 |
| | 0.2 | 26 | 128 |
| | 0.05 | 26.5 | 131 |
| Control | | 20.3 | |
| 1,4-Dihydroxy-5,8-bis[[2-(2-hydroxyethylamino)ethyl]-amino]anthraquinone dihydrochloride | 0.1 | 32 | 158 |
| 1,4-Dihydroxy-5,8-bis[[2-[2-(1-naphthyl)-3-oxazolidinyl]-ethyl]amino]anthraquinone | 3 | 42 | 195 |
| | 0.8 | 32 | 149 |
| (2nd test) | 0.2 | 27 | 126 |

TABLE II-continued

Melanotic Melanoma B16

| Compound | Dose mg./kg. | Median Survival Time (Days) | T/C × 100 (Percent) |
|---|---|---|---|
| Control | | 21.5 | |
| 1,4-Dihydroxy-5,8-bis[[2-(2-hydroxyethylamino)ethyl]-amino]anthraquinone dihydrochloride | 0.1 | 32 | 149 |
| 1,4-Dihydroxy-5,8-bis[[2-[2-(4-pyridyl)-3-oxazolidinyl]-ethyl]amino]anthraquinone | 12 | >60 | >296 |
| | 3 | 44.5 | 219 |
| | 0.8 | 26.5 | 131 |
| | 0.2 | 26 | 128 |
| Control | | 20.3 | |
| 1,4-Dihydroxy-5,8-bis[[2-(2-hydroxyethylamino)ethyl]-amino]anthraquinone dihydrochloride | 0.1 | 32 | 158 |
| 1,4-Dihydroxy-5,8-bis[[2-[2-(pentafluorophenyl)-3-oxazolidinyl]ethyl]amino]anthraquinone (1st test) | 100 | 13 | 68 |
| | 25 | 39 | 205 |
| | 6 | >55 | >289 |
| | 1.5 | >60 | >316 |
| Control | | 19.0 | |
| 1,4-Dihydroxy-5,8-bis[[2-(2-hydroxyethylamino)ethyl]-amino]anthraquinone dihydrochloride | 0.1 | 31.5 | 166 |
| 1,4-Dihydroxy-5,8-bis[[2-[2-(pentafluorophenyl)-3-oxazolidinyl]ethyl]amino]anthraquinone (2nd test) | 6 | 45 | 211 |
| | 1.5 | >52 | >244 |
| | 0.4 | 32 | 150 |
| | 0.1 | 31 | 146 |
| Control | | 21.3 | |
| 1,4-Dihydroxy-5,8-bis[[2-(2-hydroxyethylamino)ethyl]-amino]anthraquinone dihydrochloride | 0.025 | 33.0 | 155 |
| 1,4-Bis[[2-[2-(2-chloro-5-nitrophenyl)-3-oxazolidinyl]-ethyl]amino]-5,8-dihydroxyanthraquinone | 12 | >60 | >267 |
| | 3 | 47 | 209 |
| | 0.8 | 43 | 191 |
| Control | | 22.5 | |
| 1,4-Dihydroxy-5,8-bis[[2-(2-hydroxyethylamino)ethyl]-amino]anthraquinone dihydrochloride | 0.025 | 40.5 | 180 |
| 1,4-Bis[[2-[2-(5-chloro-2-nitrophenyl)-3-oxazolidinyl]-ethyl]amino]-5,8-dihydroxyanthraquinone | 12 | >60 | >267 |
| | 3 | 48.5 | 216 |
| | 0.8 | 32.5 | 144 |
| Control | | 22.5 | |
| 1,4-Dihydroxy-5,8-bis[[2-(2-hydroxyethylamino)ethyl]-amino]anthraquinone dihydrochloride | 0.025 | 40.5 | 180 |
| 1,4-Bis[[2-[2-(2,6-dichlorophenyl)-3-oxazolidinyl]ethyl]-amino]-5,8-dihydroxyanthraquinone | 50 | 44 | 196 |
| | 12 | >60 | >267 |
| | 3 | >60 | >267 |
| | 0.8 | 41 | 182 |
| Control | | 22.5 | |
| 1,4-Dihydroxy-5,8-bis[[2-(2-hydroxyethylamino)ethyl]-amino]anthraquinone dihydrochloride | 0.025 | 40.5 | 180 |
| 1,4-Dihydroxy-5,8-bis[[2-[2-(2-methylphenyl)-3-oxazolidinyl]ethyl]amino]anthraquinone | 3 | 47.5 | 211 |
| | 0.8 | >60 | >267 |
| Control | | 22.5 | |
| 1,4-Dihydroxy-5,8-bis[[2-(2-hydroxyethylamino)ethyl]-amino]anthraquinone dihydrochloride | 0.025 | 40.5 | 180 |
| 1,4-Bis[[2-[2-(3-bromophenyl)-3-oxazolidinyl]ethyl]-amino]-5,8-dihydroxyanthraquinone | 12 | 14 | 62 |
| | 3 | >60 | >267 |
| | 0.8 | >60 | >267 |
| Control | | 22.5 | |
| 1,4-Dihydroxy-5,8-bis[[2-(2-hydroxyethylamino)ethyl]-amino]anthraquinone dihydrochloride | 0.025 | 40.5 | 180 |
| 1,4-Dihydroxy-5,8-bis[[2-[2-[3-(trifluoromethyl)phenyl]-3-oxazolidinyl]ethyl]amino]-anthraquinone (1st test) | 1.5 | >57.5 | >245 |
| Control | | 23.5 | |
| 1,4-Dihydroxy-5,8-bis[[2-(2-hydroxyethylamino)ethyl]amino]anthraquinone dihydrochloride | 0.1 | 36 | 153 |
| 1,4-Dihydroxy-5,8-bis[[2-[2-[3-(trifluoromethyl)phenyl]-3-oxazolidinyl]ethyl]amino]-anthraquinone (2nd test) | 3.0 | >60 | >276 |
| | 1.5 | >46 | >212 |
| | 0.8 | 43 | 198 |
| | 0.4 | 28 | 129 |
| Control | | 21.7 | |
| 1,4-Dihydroxy-5,8-bis[[2-(2-hydroxyethylamino)ethyl]amino]anthraquinone dihydrochloride | 0.1 | 42 | 194 |
| 1,4-Bis[[2-[2-[4-(dimethylamino)phenyl]-3-oxazolidinyl]ethyl]amino]-5,8-dihydroxy-anthraquinone (1st test) | 1.5 | >54 | >251 |
| Control | | 21.5 | |
| 1,4-Dihydroxy-5,8-bis[[2-(2-hydroxyethylamino)ethyl]amino]anthraquinone dihydrochloride | 0.1 | 40 | 186 |

TABLE II-continued

| | Melanotic Melanoma B16 | | |
|---|---|---|---|
| Compound | Dose mg./kg. | Median Survival Time (Days) | T/C × 100 (Percent) |
| 1,4-Bis[[2-[2-[4-(dimethylamino)phenyl]-3-oxazolidinyl]ethyl]amino]-5,8-dihydroxy-anthraquinone (2nd test) | 1.5 0.4 | 42 43 | 198 203 |
| Control | | 21.2 | |
| 1,4-Dihydroxy-5,8-bis[[2-[2-hydroxy-ethylamino)ethyl]amino]anthraquinone dihydrochloride | 0.1 | 43 | 203 |

Also embraced within the purview of the present invention are therapeutic compositions of matter useful for ameliorating cancer diseases in mammals and containing the novel 1,4-bis(substituted amino)-5,8-dihydroxyanthraquinones of the present invention. This aspect of the invention includes the novel compositions of matter and the method of inducing the regression and/or palliation of leukemia and related cancers in mammals when administered in amounts ranging from about 0.075 mg. to about 300 mg. per square meter of body surface area per day. The interrelationship of dosages for animals of various sizes and species and humans (based on mg./m² of surface area) is described by Freireich, E. J., et al., Quantitative Comparison of Toxicity of Anti-cancer Agents in Mouse, Rat, Hamster, Dog, Monkey and Man, Cancer Chemother, Reg., 50, No. 4, 219–244, May 1966. A preferred dosage regimen for optimum results would be from about 3.0 mg./m²/day to about 150 mg./m²/day. Such dosage units are employed that a total of from about 0.5 mg. to about 525 mg. of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular, or subcutaneous routes.

The active compounds may be administered parenterally or intraperitoneally. Solutions or dispersions of the active compound can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorgansims.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 500 mg., with from about 10 to about 500 mg. being preferred. Expressed in proportions, the active compound is generally present in from about 0.1 to about 100 mg./ml. of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

This invention will be described in greater detail in conjunction with the following specific examples.

EXAMPLE 1

1,4-Dihydroxy-5,8-[[2-(2-phenyloxazolidin-3-yl)ethyl]amino]anthraquinone (A) A mixture of 30.0 g. of 1,4-Dihydroxy-5,8-bis-[[2-(2-hydroxyethylamino)ethyl]amino]anthraquinone dihydrochloride (prepared as described in Example 24 of U.S. Pat. No. 4,197,249) and 300 ml. of methanol is chilled in an ice bath in a Dewar flask. The mixture is saturated with ammonia gas and is allowed to stand at 0° C. for one hour with the continuous slow addition of ammonia gas and with periodic stirring. The solid is collected by filtration and washed by slurrying with five 150 ml. portions of methanol saturated with ammonia gas to give 22.9 g. of the free base, 1,4-dihydroxy-5,8-bis[[2-(2-hydroxyethylamino)ethyl]amino]anthraquinone, as blue-black micro rods, m.p. 175°–178° C.

(B) A suspension of 3.11 g. of the preceding free base in 55.0 ml. of benzene containing 2.23 g. of benzaldehyde is stirred and heated under reflux using a Dean-Stark trap. About 2.3 ml. of water is collected as distillate in the first hour, with no additional water over another hour. The hot solution is filtered from some dark-blue lamps which are washed with a minimal amount of hot benzene. The combined filtrates are concentrated and the product of the Example crystallizes on cooling. It is collected and washed with benzene to give 3.78 g. of a dark-blue solid, m.p. 162°–169° C.

EXAMPLE 2

1,4-Dihydroxy-5,8-bis[[2-(1-oxa-4-azaspiro[4.5]dec-4-yl)ethyl]amino]anthraquinone When 2.06 g. of cyclohexanone is substituted for benzaldehyde and a 4 hour reflux period is used in the procedure of Example 1(B) a 1.15 g. amount of the product of the Example is obtained as a blue-black solid, m.p. 218°–225° C.

1,4-Bis[[2-(2,2-dimethyl-3-oxazolidinyl)ethyl]amino]-5,8-dihydroxyanthraquinone A suspension of 3.11 g. of 1,4-dihydroxy-5,8-bis[[2-(2-hydroxyethylamino)ethyl]amino]anthraquinone [prepared as described in Example 1(A)] in 150 ml. of acetone is stirred and heated under rapid reflux. The condensate is returned to the flask by percolation through a dehydration system consisting of 40 g. of 4 A molecular sieves supported by a sintered glass plate. After a 24 hour reaction period the resulting solid is collected by filtration and is washed with hot acetone to give 2.77 g. of the product of the Example as a blue-black solid, m.p. 255°–256° C.

EXAMPLE 4

1,4-Bis[[2-[2-(2-furyl)-3-oxazolidinyl]ethyl]amino]-5,8-dihydroxyanthraquinone

A suspension of 3.11 g. of 1,4-dihydroxy-5,8-bis[[2-(2-hydroxyethylamino)ethyl]amino]anthraquinone [prepared as described in Example 1(A)] in 55.0 ml. of benzene containing 2.02 g. of 2-furaldehyde is stirred and heated under reflux using a Dean-Stark trap. A total of 0.2 ml. of water is collected as distillate over a 3 hour period, with no additional water after a total of 7 hours of refluxing. The hot solution is filtered, removing a small amount of blue-black solid. The filtrate is concentrated and petroleum ether is added to give a gum which slowly solidifies. The solid is collected and washed with benzene to give 2.05 g. of a blue-black solid.

A 1.92 g. amount of this solid is extracted on a fritted filter with a total of 40 ml. of dichloromethane. The filtrate is evaporated to give a brittle foamed glass. The glass is collected and washed with ether to give 1.73 g. of the product of the Example as a blue-black solid which is dried at 22°–28° C. for 3 days under reduced pressure; m.p. 82°–86° C.

EXAMPLE 5

1,4-Dihydroxy-5,8-[[2-(2-propyl-3-oxazolidinyl)ethyl]amino]anthraquinone

The general procedure of Example 1(B) is used, substituting 1.01 g. of butyraldehyde for benzaldehyde. The hot reaction solution is filtered, concentrated to a thick syrup, then agitated with 25 ml. of ether. The product crystallizes after several days. It is collected by filtration and washed with ether to give 3.22 g. of the product of the Example as a blue-black solid, m.p. 93°–98° C.

EXAMPLE 6

1,4-Dihydroxy-5,8-bis[[2-(2-methyloxazolidin-3-yl)ethyl]amino]anthraquinone

The general procedure of Example 1(B) is used substituting 0.93 g. of acetaldehyde for benzaldehyde; (The Dean-Stark trap is not used with this low boiling aldehyde). The reaction mixture is evaporated to dryness and the residue is agitated with 40 ml. of dichloromethane. The resulting solution is filtered. The filtrate is allowed to evaporate almost to dryness, then the residual solid is collected by filtration and is washed with ether to yield 3.27 g. of the desired product as a blue-black solid, m.p. 161°–168° C.

EXAMPLE 7

1,4-Dihydroxy-5,8-bis[[2-(2-pyrrolyl-3-oxazolidinyl)ethyl]amino]anthraquinone A suspension of 3.11 g. of 1,4-dihydroxy-5,8-bis[[2-(2-hydroxyethylamino)ethyl]amino]anthraquinone [prepared as described in Example 1(A)] in 55 ml. of toluene containing 2.0 g. of pyrrole-2-carboxaldehyde is stirred and refluxed as for Example 1(B). The hot solution is filtered. The filtrate is concentrated and allowed to stand at room temperature. The title compound separates as blue-black crystals.

EXAMPLE 8

1,4-Bis[[2-[2-(2,4-dimethoxyphenyl)-3-oxazolidinyl]ethyl]amino]-5,8-dihydroxyanthraquinone The general procedure of Example 1(B) is followed, substituting 3.4 g. of 2,4-dimethoxybenzaldehyde for benzaldehyde. The reaction mixture is allowed to cool and solids are removed by filtration. After evaporation of the filtrate the residual gum is covered with 20 ml. of methyl alcohol and allowed to stand for one week. The resulting solid is collected and washed with methyl alcohol to give 1.33 g. of the product of the Example as a blue-black solid, m.p. 181°–185° C.

EXAMPLES 9–26

Additional 1,4-bis[[(3-oxazolidinyl)alkyl]amino]-5,8-dihydroxyanthraquinone compounds listed in Table III have been prepared by the following general procedure. A suspension of 3.11 g. (0.007mole) of 1,4-bis[[2-(2-hydroxyethylamino)ethyl]amino]-5,8-dihydroxyanthraquinone [free base Example 1(A)] in 55 ml. of benzene, containing 0.021 mole of the desired aromatic aldehyde is stirred and heated under reflux for 2–48 hours using a Dean-Stark trap to remove by-product water. The hot solution is filtered. The desired product crystallizes after concentration or evaporation of the filtrate and/or addition of a solvent such as ether or hexane, then allowing the mixture to stand at room temperature for 2 hours to 2 weeks.

TABLE III 1,4-Bis[[(3-oxazolidinyl)alkyl]amino]-5,8-dihydroxyanthraquinones

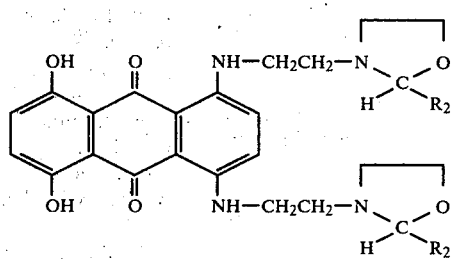

| Example | Aromatic Aldehyde | Wt. in Grams | Reflux Time in Hours | Product | $R_2$ | Product Yield in Grams | M.P. °C. |
|---|---|---|---|---|---|---|---|
| 9 | Heptaldehyde | 2.40 | 2 | 1,4-Bis[[2-(2-hexyl-3-oxazolidinyl)-ethyl]amino]-5,8-dihydroxyanthraquinone | —(CH$_2$)$_5$CH$_3$ | 3.5 | 118–120 |
| 10 | p-Anisaldehyde | 2.86 | 2 | 1,4-Dihydroxy-5,8-bis[[2-[2-(p-methoxyphenyl)-3-oxazolidinyl]ethyl]amino]anthraquinone | —C$_6$H$_4$—OCH$_3$ | 3.1 | 120–129 |
| 11 | 2-Pyridinecarboxaldehyde | 2.25 | 2 | 1,4-Dihydroxy-5,8-bis[[2-[2-(2-pyridyl)-3-oxazolidinyl]-ethyl]amino]anthraquinone | 2-pyridyl | 4.1 | 111–112 |
| 12 | 3-Pyridinecarboxaldehyde | 2.25 | 2 | 1,4-Dihydroxy-5,8-bis[[2-[2-(3-pyridyl)-3-oxazolidinyl]-ethyl]amino]anthraquinone | 3-pyridyl | 3.4 | 159–160 |
| 13 | 2-Thiophenecarboxaldehyde | 2.36 | 2 | 1,4-Dihydroxy-5,8-bis[[2-[2-(2-thienyl)-3-oxazolidinyl]-ethyl]amino]anthraquinone | 2-thienyl | 0.5 | 163–165 |
| 14 | p-Fluorobenzaldehyde | 2.61 | 2 | 1,4-Bis[[2-[2-(p-fluorophenyl)-3-oxazolidinyl]ethyl]amino]-5,8-dihydroxyanthraquinone | —C$_6$H$_4$—F | 0.6 | 195–199 |

TABLE III-continued
1,4-Bis[[(3-oxazolidinyl)alkyl]amino]-5,8-dihydroxyanthraquinones

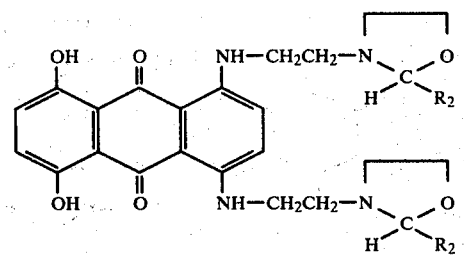

| Example | Aromatic Aldehyde | Wt. in Grams | Reflux Time in Hours | Product | R₂ | Product Yield in Grams | M.P. °C |
|---|---|---|---|---|---|---|---|
| 15 | 2-Hydroxy-p-anisaldehyde | 3.2 | 2 | 1,4-Dihydroxy-5,8-bis[[2-[2-(2-hydroxy-4-methoxyphenyl)-3-oxazolidinyl]-ethyl]amino]anthraquinone | 2-OH, 4-OCH₃ phenyl | 0.2 | 157–160 |
| 16 | 4-Benzyloxybenzaldehyde | 4.46 | 2 | 1,4-Bis[[2-[2-[p-(benzyloxy)phenyl]-3-oxazolidinyl]ethyl]amino]-5,8-dihydroxyanthraquinone | 4-OCH₂Ph phenyl | 0.7 | 185–188 |
| 17 | 3,5-Dimethoxybenzaldehyde | 3.49 | 2 | 1,4-Bis[[2-[2-(3,5-dimethoxyphenyl)-3-oxazolidinyl]ethyl]amino]-5,8-dihydroxyanthraquinone | 3,5-(OCH₃)₂ phenyl | 0.6 | 175–178 |
| 18 | Naphthaldehyde | 3.28 | 2 | 1,4-Dihydroxy-5,8-bis[[2-[2-(1-naphthyl)-3-oxazolidinyl]ethyl]amino]-anthraquinone | 1-naphthyl | 1.9 | 149–151 |
| 19 | 4-Pyridinecarboxaldehyde | 2.25 | 2 | 1,4-Dihydroxy-5,8-bis[[2-[2-(4-pyridyl)-3-oxazolidinyl]-ethyl]amino]anthraquinone | 4-pyridyl | 0.8 | 183–185 |
| 20 | Pentafluorobenzaldehyde | 4.12 | 2 | 1,4-Dihydroxy-5,8-bis[[2-[2-(pentafluorophenyl)-3-oxazolidinyl]ethyl]amino]anthraquinone | pentafluorophenyl | 4.6 | 82–84 |
| 21 | 2-Chloro-5-nitrobenzaldehyde | 3.90 | 2 | 1,4-Bis[[2-[2-(2-chloro-5-nitrophenyl)-3-oxazolidinyl]-ethyl]amino]-5,8-dihydroxyanthraquinone | 2-Cl, 5-NO₂ phenyl | 0.2 | 169–171 |
| 22 | 5-Chloro-2-nitrobenzaldehyde | 3.90 | 2 | 1,4-Bis[[2-[2-(5-chloro-2-nitrophenyl)-3-oxazolidinyl]-ethyl]amino]-5,8-dihydroxyanthraquinone | 5-Cl, 2-NO₂ phenyl | 5.40 | 149–151 |

TABLE III-continued
1,4-Bis[[(3-oxazolidinyl)alkyl]amino]-5,8-dihydroxyanthraquinones

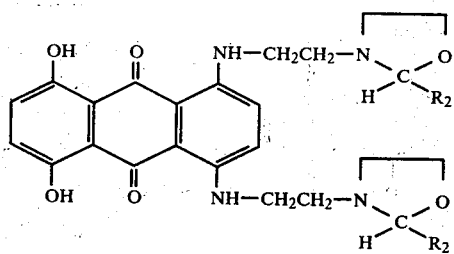

| Example | Aromatic Aldehyde | Wt. in Grams | Reflux Time in Hours | Product | $R_2$ | Product Yield in Grams | M.P. °C. |
|---|---|---|---|---|---|---|---|
| 23 | 2,6-Dichloro-benzaldehyde | 3.68 | 48 | 1,4-Bis[[2-[2-(2,6-dichlorophenyl)-3-oxazolidinyl]ethyl]-amino]-5,8-dihydroxy-anthraquinone | Cl, Cl | 4.77 | 217–220 |
| 24 | o-Tolualde-hyde | 2.52 | 3 | 1,4-Dihydroxy-5,8-bis[[2-[2-(2-methyl-phenyl)-3-oxazolidin-yl]ethyl]amino]-anthraquinone | $CH_3$ | 3.79 | 105–110 |
| 25 | 3-Bromobenz-aldehyde | 3.89 | 3 | 1,4-Bis[[2-[2-(3-bromophenyl)-3-oxazolidinyl]ethyl]-amino]5,8-dihydroxy-anthraquinone | Br | 5.22 | 160–164 |
| 26 | α,α,α-Tri-fluoro-m-tolualdehyde | 3.66 | 3 | 1,4-Dihydroxy-5,8-bis[[2-[2-[3-(tri-fluoromethyl)phenyl]-3-oxazolidinyl]eth-yl]amino]anthra-quinone | $CF_3$ | 4.83 | 154–158 |

EXAMPLE 27

1,4-Bis[[2-[2-[4-(dimethylamino)phenyl]-3-oxazolidinyl]ethyl]amino]-5,8-dihydroxyanthraquinone A suspension of 3.11 g. of 1,4-dihydroxy-5,8-bis[[2-(2-hydroxyethylamino)ethyl]amino]anthraquinone [prepared as described in Example 1(A)] in 60 ml. of toluene containing 3.13 g. of p-dimethylaminobenzaldehyde is stirred and heated at reflux for 5 hours by the procedure of Example 1(B). The hot reaction solution is filtered and is allowed to stand for several days. The crystallized product is collected by filtration and washed with toluene to yield 4.34 g. of the product of the Example as dark-blue crystals, m.p. 150°–154° C.

EXAMPLE 28

1,4-Bis[[2-[2-(4-cyanophenyl)-3-oxazolidinyl]ethyl]amino]-5,8-dihydroxyanthraquinone When 2.77 g. of 4-cyanobenzaldehyde is substituted for benzaldehyde in the general procedure of Example 1(B) the product of the Example is obtained.

EXAMPLE 29

1,4-Bis[[2-(2-ethenyl-3-oxazolidinyl)ethyl]amino]-5,8-dihydroxyanthraquinone

When 1.18 g. of acrolein is substituted for acetaldehyde in the general procedure of Example 6 the desired product is obtained.

EXAMPLE 30

1,4-Dihydroxy-5,8-bis[[3-(2-phenyloxazolidin-3-yl)propyl]amino]anthraquinone (A) 1,4-Dihydroxy-5,8-bis[[3-(2-hydroxyethylamino)propyl]amino]anthraquinone dihydrochloride (prepared as described in Example 28 of U.S. Pat. No. 4,197,249) is converted to the corresponding free base by the procedure of Example 1(A).

(B) When 3.28 g. of the preceding free base is substituted for 1,4-dihydroxy-5,8-bis[[2-(2-hydroxyethylamino)ethyl]amino]anthraquinone and condensed with 2.23 of benzaldehyde in the procedure of Example 1(B) the product of the Example is obtained.

EXAMPLE 31

1,4-Dihydroxy-5,8-bis[[2-(5-methyl-2-phenyloxazolidin-3-yl)ethyl]amino]anthraquinone (A) 1,4-Dihydroxy-5,8-bis[[2-(2-hydroxypropylamino)ethyl]amino]anthraquinone dihydrochloride (prepared as described in Example 32 of U.S. Pat. No. 4,197,249) is converted to the corresponding free base by the method of Example 1(A).

(B) Condensation of 3.28 g. of the preceding free base with 2.23 g. of benzaldehyde by the procedure of Example 1(B) gives the title compound as a blue-black solid.

EXAMPLE 32

1,4-Dihydroxy-5,8-bis[[2-(2-phenyl-5,6-dihydro-2H-1,3-oxazin-3(4H-yl)ethyl]amino]anthraquinone (A) 1,4-Dihydroxy-5,8-bis[[2-(3-hydroxypropylamino)ethyl]amino]anthraquinone dihydrochloride (prepared as described in Example 30 of U.S. Pat. No. 4,197,249) is converted to the corresponding free base by the procedure of Example 1(A).

(B) Condensation of 3.28 g. of the preceding free base with 2.23 g. of benzaldehyde by the procedure of Example 1(B) gives the title compound as a blue-black solid.

EXAMPLE 33

Preparation of Parenteral Suspension

In a solution of 700 ml. of propylene glycol and 200 ml. of water for injection is suspended 20.0 g. of 1,4-dihydroxy-5,8-bis[[2-(2-phenyloxazolidin-3-yl)ethyl]amino]anthraquinone with stirring. After suspension is complete, the volume is made up to 1000 ml. with water for injection. The formulation is sterilized, filled into 5.0 ml. ampoules each containing 2.0 ml. (representing 40 mg. of drug) and sealed under nitrogen.

EXAMPLE 34

Preparation of Parenteral Suspension

The active compound in powder form is sterilized by ethylene oxide sterilization. The sterilized powder is aseptically filled into vials in dosage unit form and the vials are sealed. Immediately prior to use the powder is suspended by the addition of a suitable sterile diluent. The resulting suspension may be sonicated if necessary to promote dispersion. (This mode of suspension of advantageous for compounds which might undergo some hydrolysis on long standing in an aqueous medium.)

I claim:

1. A compound selected from the group consisting of those of the formula:

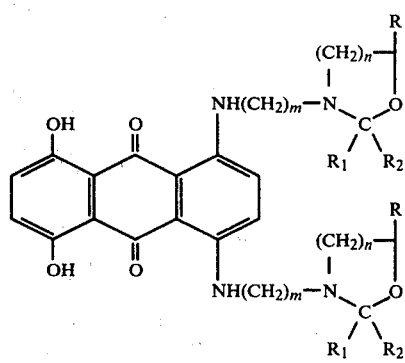

wherein m is the integer 2 or 3; n is the integer 1 or 2; R is hydrogen or methyl; $R_1$ is hydrogen or methyl; and $R_2$ is alkyl ($C_1$-$C_6$), ethenyl, 2-pyridyl, 3-pyridyl, 4-pyridyl, 2-thienyl, 3-thienyl, 2-furyl, 3-furyl, 2-pyrrolyl, 3-pyrrolyl, 1-naphthyl, 2-naphthyl, pentafluorophenyl or moieties of the formula:

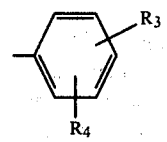

wherein $R_3$ and $R_4$ may be the same or different and are hydrogen, fluoro, chloro, bromo, hydroxy, methoxy, methyl, benzyloxy, cyano, amino, nitro or trifluoromethyl; and $R_1$ and $R_2$ taken together is alkylene ($C_2$-$C_6$); and the pharmacologically acceptable acid-addition salts thereof.

2. A compound selected from the group consisting of those of the formula:

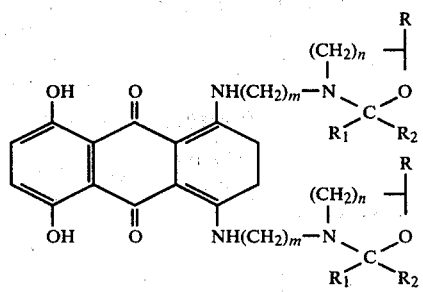

wherein m is the integer 2 or 3; n is the integer 1 or 2; R is hydrogen or methyl; $R_1$ is hydrogen or methyl; and $R_2$ is alkyl ($C_1$-$C_6$), ethenyl, 2-pyridyl, 3-pyridyl, 4-pyridyl, 2-thienyl, 3-thienyl, 2-furyl, 3-furyl, 2-pyrrolyl, 3-pyrrolyl, 1-naphthyl, 2-naphthyl, pentafluorophenyl or moieties of the formula:

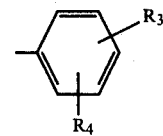

wherein $R_3$ and $R_4$ may be the same or different and are hydrogen, fluoro, chloro, bromo, hydroxy, methoxy, methyl, benzyloxy, cyano, amino, nitro or trifluoromethyl; and $R_1$ and $R_2$ taken together is alkylene ($C_2$–$C_6$); the tautomers thereof and the pharmacologically acceptable acid-addition salts thereof.

3. The compound according to claim 1, 1,4-dihydroxy-5,8-bis[[2-(2-phenyloxazolidin-3-yl)ethyl]amino]anthraquinone.

4. The compound according to claim 1, 1,4-dihydroxy-5,8-bis[[2-(1-oxa-4-azaspiro[4.5]dec-4-yl)ethyl]amino]anthraquinone.

5. The compound according to claim 1, 1,4-bis[[2-(2,2-dimethyl-3-oxazolidinyl)ethyl]amino]-5,8-dihydroxyanthraquinone.

6. The compound according to claim 1, 1,4-bis[[2-[2-(2-furyl)-3-oxazolidinyl]ethyl]amino]-5,8-dihydroxyanthraquinone.

7. The compound according to claim 1, 1,4-dihydroxy-5,8-bis[[2-(2-propyl-3-oxazolidinyl)ethyl]amino]anthraquinone.

8. The compound according to claim 1, 1,4-dihydroxy-5,8-bis[[2-(2-methyloxazolidin-3-yl)ethyl]amino]anthraquinone.

9. The compound according to claim 1, 1,4-dihydroxy-5,8-bis[[2-(2-pyrrolyl)-3-oxazolidinyl)ethyl]amino]anthraquinone.

10. The compound according to claim 1, 1,4-bis[[2-[2-(2,4-dimethoxyphenyl)-3-oxazolidinyl]ethyl]amino]-5,8-dihydroxyanthraquinone.

11. The compound according to claim 1, 1,4-bis[[2-(2-hexyl-3-oxazolidinyl)ethyl]amino]-5,8-dihydroxyanthraquinone.

12. The compound according to claim 1, 1,4-dihydroxy-5,8-bis[[2-[2-(p-methoxyphenyl)-3-oxazolidinyl]ethyl]amino]anthraquinone.

13. The compound according to claim 1, 1,4-dihydroxy-5,8-bis[[2-[2-(2-pyridyl)-3-oxazolidinyl]ethyl]amino]anthraquinone.

14. The compound according to claim 1, 1,4-dihydroxy-5,8-bis[[2-[2-(3-pyridyl)-3-oxazolidinyl]ethyl]amino]anthraquinone.

15. The compound according to claim 1, 1,4-dihydroxy-5,8-bis[[2-[2-(2-thienyl)-3-oxazolidinyl]ethyl]amino]anthraquinone.

16. The compound according to claim 1, 1,4-bis[[2-[2-(p-fluorophenyl)-3-oxazolidinyl]ethyl]amino]-5,8-dihydroxyanthraquinone.

17. The compound according to claim 1, 1,4-dihydroxy-5,8-bis[[2-[2-(2-hydroxy-4-methoxyphenyl)-3-oxazolidinyl]ethyl]amino]anthraquinone.

18. The compound according to claim 1, 1,4-bis[[2-[2-[p-(benzyloxy)phenyl]-3-oxazolidinyl]ethyl]amino]-5,8-dihydroxyanthraquinone.

19. The compound according to claim 1, 1,4-bis[[2-[2-(3,5-dimethoxyphenyl)-3-oxazolidinyl]ethyl]amino]-5,8-dihydroxyanthraquinone.

20. The compound according to claim 1, 1,4-dihydroxy-5,8-bis[[2-[2-(1-naphthyl)-3-oxazolidinyl]ethyl]amino]anthraquinone.

21. The compound according to claim 1, 1,4-dihydroxy-5,8-bis[[2-[2-(4-pyridyl)-3-oxazolidinyl]ethyl]amino]anthraquinone.

22. The compound according to claim 1, 1,4-dihydroxy-5,8-bis[[2-[2-(pentafluorophenyl)-3-oxazolidinyl]ethyl]amino]anthraquinone.

23. The compound according to claim 1, 1,4-bis[[2-[2-(2-chloro-5-nitrophenyl)-3-oxazolidinyl]ethyl]amino]-5,8-dihydroxyanthraquinone.

24. The compound according to claim 1, 1,4-bis[[2-[2-(5-chloro-2-nitrophenyl)-3-oxazolidinyl]ethyl]amino]-5,8-dihydroxyanthraquinone.

25. The compound according to claim 1, 1,4-bis[[2-[2-(2,6-dichlorophenyl)-3-oxazolidinyl]ethyl]amino]-5,8-dihydroxyanthraquinone.

26. The compound according to claim 1, 1,4-dihydroxy-5,8-bis[[2-[2-(2-methylphenyl)-3-oxazolidinyl]ethyl]amino]anthraquinone.

27. The compound according to claim 1, 1,4-bis[[2-[2-(3-bromophenyl)-3-oxazolidinyl]ethyl]amino-5,8-dihydroxyanthraquinone.

28. The compound according to claim 1, 1,4-dihydroxy-5,8-bis[[2-[2-[3-(trifluoromethyl)phenyl]-3-oxazolidinyl]ethyl]amino]anthraquinone.

29. The compound according to claim 1, 1,4-bis[[2-[2-[4-(dimethylamino)phenyl]-3-oxazolidinyl]ethyl]amino]anthraquinone.

30. The compound according to claim 1, 1,4-bis[[2-[2-(4-cyanophenyl)-3-oxazolidinyl]ethyl]amino]-5,8-dihydroxyanthraquinone.

31. The compound according to claim 1, 1,4-bis[[2-(2-ethenyl-3-oxazolidinyl)ethyl]amino]-5,8-dihydroxyanthraquinone.

32. The compound according to claim 1, 1,4-dihydroxy-5,8-bis[[3-(2-phenyloxazolidin-3-yl)propyl]amino]anthraquinone.

33. The compound according to claim 1, 1,4-dihydroxy-5,8-bis[[2-(5-methyl-2-phenyloxazolidin-3-yl)ethyl]amino]anthraquinone.

34. The compound according to claim 1, 1,4-dihydroxy-5,8-bis[[2-[2-(2-naphthyl)-3-oxazolidinyl]ethyl]amino]anthraquinone.

35. The compound according to claim 2, leuco 1,4-dihydroxy-5,8-bis[[2-[2-phenyl-5,6-dihydro-2H-1,3-oxazin-3-(4H-yl)]ethyl]amino]anthraquinone.

36. The method of inducing regression of leukemia and/or inhibiting growth of tumors in a mammal comprising administering to said mammal an effective amount of a compound selected from the group consisting of those of claim 1 or 2.

37. A pharmaceutical composition in dosage unit form comprising from about 0.075 mg./m$^2$ to about 300 mg./m$^2$ of body surface area of a compound selected from the group consisting of those of claim 1 or 2.

* * * * *